United States Patent [19]

Fajnsztajn

[11] Patent Number: 4,656,675
[45] Date of Patent: Apr. 14, 1987

[54] VENTED URINARY DRAINAGE DEVICE

[76] Inventor: Aleksander Fajnsztajn, 555 Kernberry Dr., San Rafael, Calif. 94903

[21] Appl. No.: 862,315

[22] Filed: May 12, 1986

[51] Int. Cl.⁴ .................. A47K 11/00; A61F 5/44; A61B 5/00; A61M 1/06
[52] U.S. Cl. .................. 4/144.4; 4/144.3; 128/760; 128/767; 604/73; 604/349; 604/350; 604/352
[58] Field of Search ............... 4/144.1, 301; 604/352, 604/350, 349, 35, 73, 131, 181, 380; 128/767, 760

Primary Examiner—Henry K. Artis
Attorney, Agent, or Firm—Alfons Puishes

[57] ABSTRACT

A safe, effective, sanitary device for draining of urine from a male patient which prevents spillage of the urine while preserving the comfort of the patient. The device is made of an elastomeric material which fits around the penis and leads to an exit tube which in turn leads to a suitable receptacle. The device is a vent critically located at a point close to the discharge from the penis and above the exit tube. The vent is covered with a membrane which permits the passage of air but prevents the passage of urine.

4 Claims, 6 Drawing Figures

U.S. Patent    Apr. 14, 1987    4,656,675
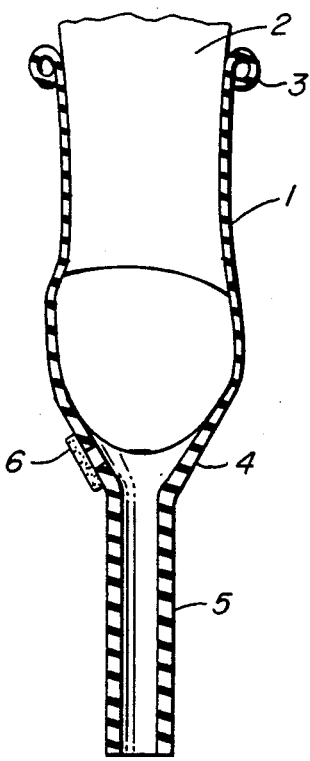
FIG._1.
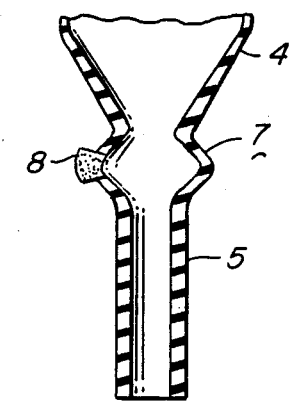
FIG._2.
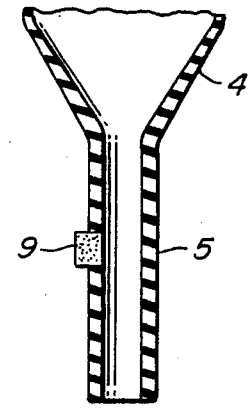
FIG._3.
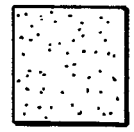
FIG._4.
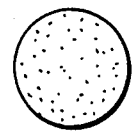
FIG._5.
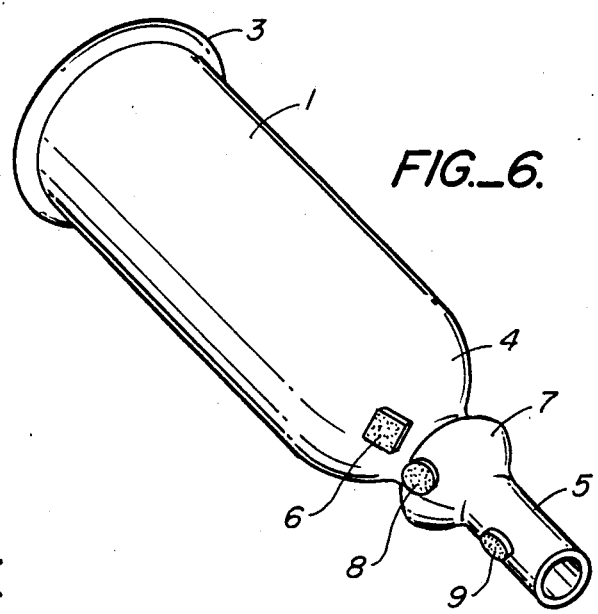
FIG._6.

VENTED URINARY DRAINAGE DEVICE

BACKGROUND OF THE INVENTION

Removal of urine from a male patient in a convenient, effective, comfortable and sanitary manner has been a long standing problem.

A number of devices have been constructed to attempt to solve this problem. These usually take the basic form of an elastic shield of the nature of a condom which is disposed to fit over the penis and has an outlet spout or nozzle at its end which may be connected to a suitable receptacle, the latter being vented to the atmosphere. These are set forth below.

Helmreid, U.S. Pat. No. 4,388,923 shows the basic elements as above and in addition a seal to effect tight connection between the penis and the connecting section of the collector.

Izumi, U.S. Pat. No. 4,366,818 discloses a vacuum device connected to the collector and actuated by the urine level in the receptacle to facilitate removal of the urine.

Walker, U.S. Pat. No. 3,800,795 is an improvement in the collecting receptacle which comprises improved venting means in the receptacle.

Izumi, U.S. Pat. No. 4,443,217 is a divisional of his U.S. Pat. No. 4,366,818 above, being an improvement in the control of the vacuum section.

Alexander, U.S. Pat. No. 4,378,018 shows an improved method of fastening the basic collector to the penis.

Rogers III, U.S. Pat. No. 3,835,857 discloses a collector of certain dimensional combinations to facilitate its operation and also detachable couplings to the receptacle tank.

While some of the prior art teaches incorporation of vents in the receptacle, none except Rogers provide for a vent close to the urine source to prevent backing up of the urine against the penis. Rogers does show small vents in the collector but there is no insurance against the outflow of urine as well as air through them. This is what I have sought to prevent in my invention.

SUMMARY OF THE INVENTION

I have discovered that by installing a novel vent at a critical point in the collector I am able to overcome the objections and problems encountered by all previous drainage or collecting devices in a very simple manner. For my vent I utilize a material which permits air to flow through, but is practically impervious to liquid at pressures encountered here. I locate my vent in the elastic collector at a point close to the source of the urine formed in the removal tube or exit nozzle from the collector proper. This permits free flow of urine into a vented receptacle and prevents backing up against the penis.

DESCRIPTION OF THE DRAWINGS

FIG. 1 is a vertical section through my device shown in position on a penis and shows the location of my vent.

FIG. 2 is an alternate embodiment using a bulbous section in the exit nozzle or tube with my vent located thereon.

FIG. 3 shows a regular exit nozzle or tube with the vent located thereon.

FIG. 4 shows a schematic of my vent having a square or rectangular configuration.

FIG. 5 shows a schematic of my vent having a circular configuration.

FIG. 6 shows an isometric view of my device in partially unrolled form prior to application to a patient, and showing alternate locations of my vent.

DESCRIPTION OF A PREFERRED EMBODIMENT

Referring now to the figures there is seen my device 1 in position on a penis, seen schematically at 2. My device is made of thin elastic or elastomeric material, rubber, latex, etc., capable of being rolled onto the penis after the manner of condom as indicated by the rolled edge 3.

A conical section of my collector is shown at 4 which is joined to exit nozzle or tube 5 of thicker material having an inside diameter of the order of one-quarter of an inch. The latter is disposed for connection to a suitable vented receptacle which may be a rubber bag or other means.

My filter shown schematically at 6 is positioned on the conical section 4 over my vent which places it above the tube 5 and clear of the end of penis 2. My filter is a relatively thin porous membrane which permits it to pass through but is practically impervious to liquids at ordinary pressures, similar to type TF-200 of polytetrafluorethylene or similar material as manufactured by Gelman Sciences, Inc., of Ann Arbor, Mich. This membrane is bonded to the body of my device by any suitable means. I have discovered that a filter having a pore size of 0.2 mils and an area of approximately 0.0625 square inches represents a critical combination for good operation of such a device.

In some cases it may be desirable to make my exit nozzle or tube 5 with a bulbous section 7 in which case my vent 8 is positioned thereon, (FIG. 2). For manufacturing simplicity I may also locate my vent 9 directly on the tube 5 as shown on FIG. 3, although this is not so effective.

The membranes may be circular, square or rectangular as indicated diagrammatically on FIGS. 4 and 5. This is for manufacturing convenience.

Under the combination approximately as set forth above the device provides comfort for the patient while facilitating removal of the urine without spilling to the exterior.

I claim:

1. An improved urinary drainage device for removal of urine from a male patient comprising:
   a sheath of thin elastic material comprising:
      a thin cylindrical section disposed for rolling into position tightly upon a penis;
      a frusto-conical section attached at its larger end to one end of said cylindrical section and forming an integral part of said sheath;
      a hollow cylindrical tube of thicker material than said sheath attached to the smaller end of said frusto-conical section;
      a vent positioned on said frusto-conical section;
      said vent having an area approximately equivalent to the area of the inside of said tube;
      said vent being covered by a membrane capable of passing air therethrough but being impervious to liquid at relatively low pressures.

2. The device of claim 1 in which said cylindrical tube includes a bulbous section therein;
   said vent being positioned on said bulbous section.

3. The device of claim 1 in which said vent is positioned on said cylindrical tube.

4. The device of claim 1 in which said vent comprises a membrane having a pore size of 0.2 mils and a vent area of the order of 0.0625 square inches when said tube has an internal diameter of the order of 0.25 inches.

* * * * *